(12) United States Patent
Potter

(10) Patent No.: US 8,162,934 B2
(45) Date of Patent: Apr. 24, 2012

(54) MEDICAL CATHETER ASSEMBLY WITH DEFLECTION PULL RING AND DISTAL TIP INTERLOCK

(75) Inventor: Daniel J. Potter, Stillwater, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1158 days.

(21) Appl. No.: 11/963,441

(22) Filed: Dec. 21, 2007

(65) Prior Publication Data

US 2009/0163917 A1 Jun. 25, 2009

(51) Int. Cl.
*A61B 18/14* (2006.01)
(52) U.S. Cl. ............ 606/41; 606/34; 606/32; 604/95.04
(58) Field of Classification Search .................... 606/41, 606/32–34, 47, 50, 129; 604/95.01
See application file for complete search history.

(56) References Cited

U.S. PATENT DOCUMENTS

| | | | |
|---|---|---|---|
| 5,273,535 A | 12/1993 | Edwards et al. | |
| 5,389,073 A | 2/1995 | Imran | |
| 5,391,147 A | 2/1995 | Imran et al. | |
| 5,431,168 A | 7/1995 | Webster et al. | |
| 5,462,527 A | 10/1995 | Stevens-Wright et al. | |
| 5,478,330 A | 12/1995 | Imran et al. | |
| 5,533,967 A | 7/1996 | Imran | |
| 5,545,200 A | 8/1996 | West et al. | |
| 5,588,964 A | 12/1996 | Imran et al. | |
| 5,666,970 A | 9/1997 | Smith | |
| 5,882,333 A * | 3/1999 | Schaer et al. | 604/95.01 |
| 5,968,052 A * | 10/1999 | Sullivan et al. | 623/1.11 |
| 6,113,572 A * | 9/2000 | Gailey et al. | 604/93.01 |
| 6,926,669 B1 * | 8/2005 | Stewart et al. | 600/439 |
| 7,229,437 B2 | 6/2007 | Johnson et al. | |

(Continued)

FOREIGN PATENT DOCUMENTS

EP 0982047 3/2000
(Continued)

OTHER PUBLICATIONS

International Search Report and Written Opinion for PCT/US2008/083731 mailed Jan. 9, 2009.

*Primary Examiner* — Linda C Dvorak
*Assistant Examiner* — Amanda Scott
(74) *Attorney, Agent, or Firm* — Dykema Gossett PLLC

(57) ABSTRACT

A medical catheter assembly includes a deflectable catheter shaft, a distal tip with tip element and a mounting shaft, and a pull ring assembly, the distal tip defining guide channels through which pull wires of the pull ring assembly pass such that the pull wires will initially extend from the pull ring toward the tip element and then loop back toward and through the catheter shaft and to a handle actuator. Pulling of the pull wires by the handle actuator to tilt the pull ring and deflect the catheter shaft will cause the pull ring to move toward tip element. The pull ring and tip element are thus interlocked. Stress forces on the connection joints between the pull wires and the pull ring will be dissipated, reducing the incidence of failure of the pull ring assembly. The medical catheter can be a non-irrigated ablation catheter wherein the tip element is a tip electrode, or an irrigated ablation catheter wherein the tip element is a tip electrode and a fluid manifold.

22 Claims, 4 Drawing Sheets

U.S. PATENT DOCUMENTS

| | | | |
|---|---|---|---|
| 7,632,265 B2 * | 12/2009 | Hauck et al. | 606/34 |
| 7,974,674 B2 * | 7/2011 | Hauck et al. | 600/374 |
| 2003/0078571 A1 * | 4/2003 | Sliwa et al. | 606/28 |
| 2006/0015096 A1 * | 1/2006 | Hauck et al. | 606/41 |
| 2007/0016167 A1 | 1/2007 | Smith et al. | |
| 2007/0250056 A1 | 10/2007 | Vanney | |
| 2007/0270679 A1 | 11/2007 | Nguyen et al. | |

FOREIGN PATENT DOCUMENTS

| | | |
|---|---|---|
| EP | 1205208 | 5/2002 |
| WO | WO-97/29801 | 8/1997 |

* cited by examiner

MEDICAL CATHETER ASSEMBLY WITH DEFLECTION PULL RING AND DISTAL TIP INTERLOCK

BACKGROUND OF THE INVENTION

1. Field of Invention

The present invention relates to medical catheter assemblies, and in particular to medical catheter assemblies which utilize a deflection pull ring adjacent a distal tip at the distal end of the catheter shaft to bend the deflectable catheter shaft and move the distal tip in a desired direction.

2. The Prior Art

Medical catheter assemblies used in the diagnosis or treatment of various medical abnormalities are in common use in medical facilities throughout the world. They generally include a deflectable catheter shaft that can be inserted in and extended along a suitable vein or artery of person being diagnosed or treated to a desired site; a handle actuator which supports a proximal end of the catheter shaft; a distal tip which is connected to the distal end of the catheter shaft and which includes a specialized tip element for the appropriate diagnosis or treatment; and a pull ring assembly which includes a pull ring near the distal end of the catheter shaft and pull wires which extend from the pull ring through the catheter shaft back to the handle actuator for tilting or rocking the pull ring upon manual operation of the handle actuator and consequential pulling of the pull wires, i.e., for deflecting a distal end portion of the catheter shaft with distal tip in a desired direction.

Ablation catheter assemblies are a category of medical catheter assembly used to ablate tissue, e.g., in the treatment of heart malfunctions. They can be irrigated (discharge ablation fluid in addition to ablation energy) or non-irrigated (discharge of ablation energy but not fluid). The distal tip will include a tip electrode as the specialized tip element and an energy source will be connected to their handle actuator to supply energy to the tip electrode. In irrigated catheter assemblies a fluid manifold is attached to, or is one-piece with, the tip electrode, and a fluid source is attached to their handle actuator to supply ablation fluid thereto. In either, the distal tip can include a mounting shaft which cooperates with the distal end of the adjacent deflectable catheter shaft for connection thereto.

It has been found that the operation of such medical catheter assemblies, including irrigated or non-irrigated ablation catheter assemblies, can become compromised over time with creeping of the pull ring towards the handle actuator (and away from the distal tip) due to repeated tilting or rocking thereof by the pull wires. In addition, failure of the medical catheter assemblies can occur with separation of the pull wires from the pull rings of the pull ring assemblies due to stress failure of the braze or weld joints therebetween.

It is thus an object of the present invention to provide a medical catheter assembly (including an irrigated or non-irrigated ablation catheter assembly) which is constructed such that creeping of the pull ring towards the handle actuator (and away from the distal tip) is prevented.

It is another object of the present invention to provide a medical catheter assembly (including an irrigated or non-irrigated catheter assembly) which is constructed such that stress on the connecting joints between the pull wires and pull ring is reduced, reducing failure of medical catheter assembly due to failure of the pull ring assembly.

SUMMARY OF INVENTION

These and other objects are achieved with a medical catheter assembly wherein the distal tip is constructed to include guide channels for the pull wires of the pull wire assembly such that the pull wires will initially extend from the pull ring to the which they are attached towards the tip element (in the case of an irrigated or non-irrigated ablation catheter assembly a tip electrode), and then loop back toward and through the catheter shaft via the guides channels to the handle actuator. This creates a distal tip and pull ring interlock. Such a construction results in the pull ring of the pull ring assembly being moved towards the tip element with operation (pulling) of the pull wires. It also results in dissipated (reduced) forces applied to the braze or weld connecting the pull wires to the pull ring such that failure of the pull ring assembly will only occur near the tensile stress limit of the pull wires themselves.

The invention will be better understood by reference to the attached drawings, taken in conjunction with the following discussion.

DETAILED DESCRIPTION OF THE PREFERRED EMBODIMENTS

Figure 1:
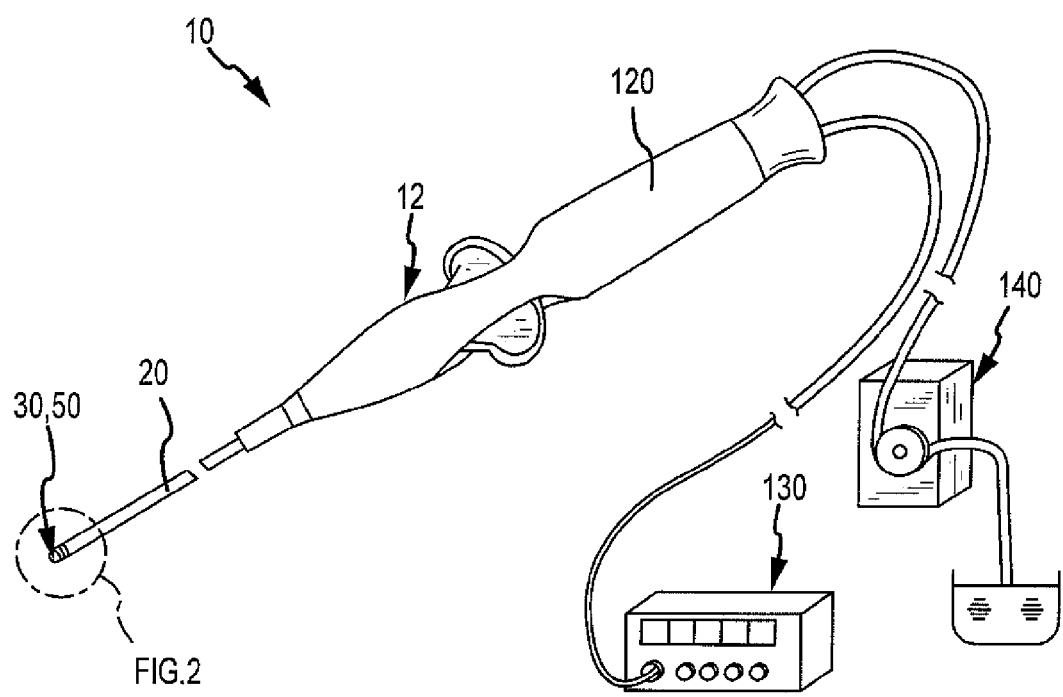
FIG. 1 is an isometric view of an irrigated ablation catheter system that includes an ablation catheter assembly, an energy source and a fluid source in accordance with a first embodiment of the present invention.

FIG. 1 shows an irrigated ablation catheter system 10 according to a preferred embodiment of the present invention. It includes an irrigated ablation catheter assembly 12 connected to an energy source 130 and a fluid source 140.

The irrigated ablation catheter assembly 12 includes a catheter 20, a handle actuator 120 which supports a proximate end of the catheter 20, a distal tip 30 attached to a distal end of the catheter and a pull ring assembly 50.

Figure 2:
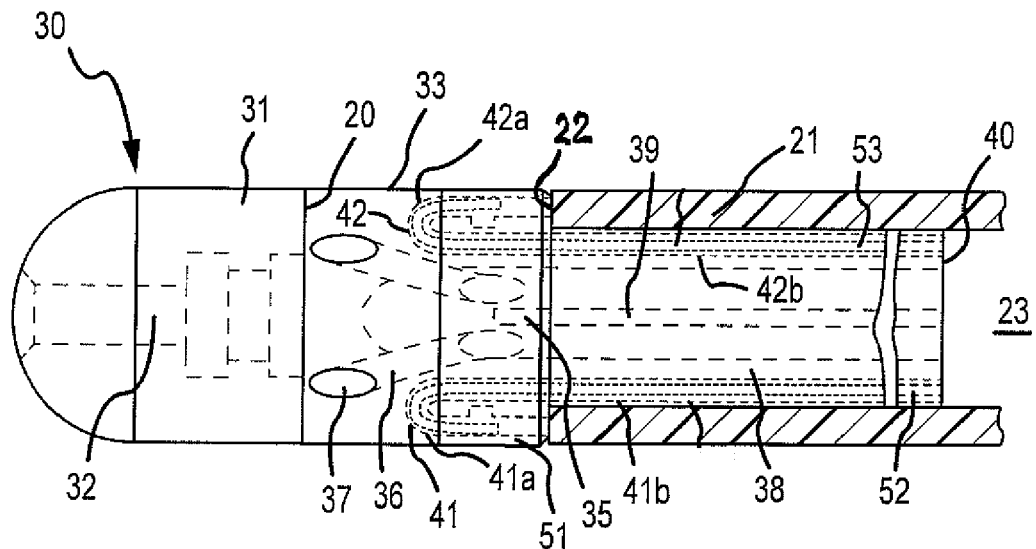
FIG. 2 is an enlarged side view of the distal end portion of the deflectable ablation catheter shaft, the pull ring assembly and distal tip of the catheter of FIG. 1.
Figure 3:
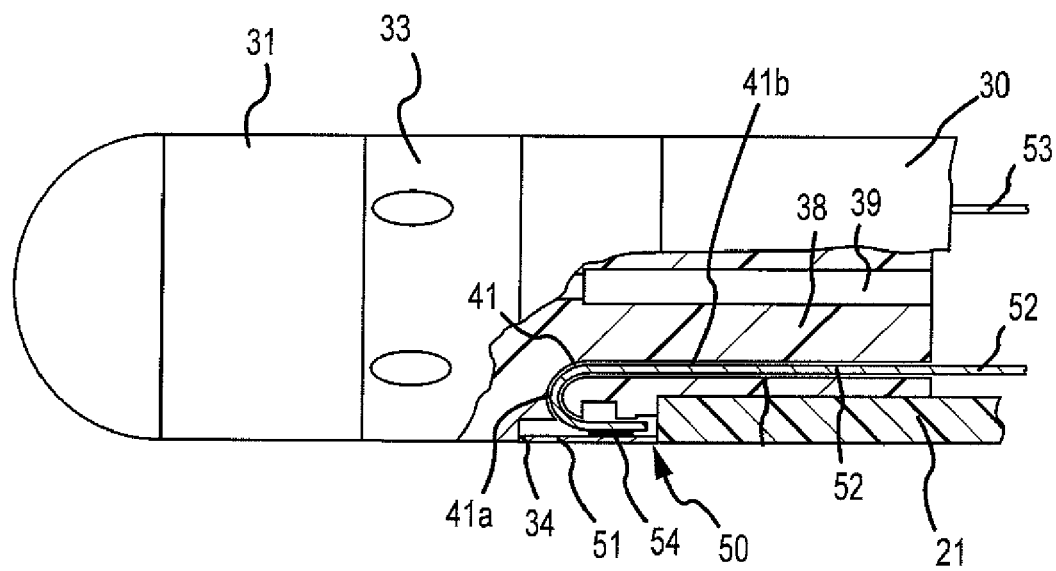
FIG. 3 is an enlarged detail of FIG. 2.

As seen in FIGS. 2 and 3, the distal tip 30 includes a tip electrode 31, a fluid manifold 33 and a mounting shaft 38. The fluid manifold 33 is attached to the tip electrode with adhesive (in another embodiment the fluid manifold and the tip electrode can be one piece). The mounting shaft 38 is one piece with the fluid manifold 33, and it extends into the hollow interior 23 of the catheter shaft 21. It has a smaller diameter than that of the fluid manifold (which is cylindrical in shape), thus leaving an outer annular ledge 34 on a rear face of the fluid manifold. The mounting shaft defines a central axial passageway 39 for ablation fluid supplied by a fluid delivery tube (not shown) in the catheter shaft. The fluid manifold 33 defines a central axial passageway 35 which is an extension of the central axial passageway 39, and delivery channels 36 that extend from the axial passageway 35 to orifices 37 spaced around its periphery (in another embodiment only one delivery channel leading to one orifice is employed). Fluid supplied to the axial passageway 39 in the mounting shaft will flow to the axial passageway 35 and then through delivery channels 36 to orifices 37 for discharge around the distal tip. The tip electrode 31 includes a channel 32 which will deliver fluid from the axial passageway 35 to its distal end. It can be made of platinum or other well-known materials.

Guide channels 41 and 42 are provided in the mounting shaft 38 at diametrically-opposed locations. The guide channel 41 includes a curved section 41a and a rectilinear section 41b. The curved section 41a has an inlet opening in the outer surface of the mounting shaft near fluid manifold 33 and the rectilinear section 41b has an outlet opening at the free end 40 of the mounting shaft. The guide channel 42 has corresponding sections 42a and 42b. The pull wires of the pull ring assembly respectively extend through these guide channels.

The pull ring assembly 50 includes a pull ring 51 and pull wires 52 and 53 attached to diametrically opposite locations on an inner face of the pull ring by a solder or weld joint 54. The pull wires are flat along at least a portion of their length, in particular at their distal ends, otherwise round. Other configurations are possible. The pull ring 51 is positioned between the distal end 22 of the catheter shaft 21 and the outer annular ledge 34 of the fluid manifold, and the pull wires extend from the pull ring toward the fluid manifold and then loop back respectively in and through the guide channels 41 and 42 to the handle actuator 120. Pulling of the pull wires 52, 53 by the handle actuator during use of the catheter assembly will cause the pull ring to tilt or rock, thereby bending the catheter shaft 21, and also pulling the pull ring 51 toward contact with the outer annular ledge 34 of the fluid manifold 33.

Figure 4:
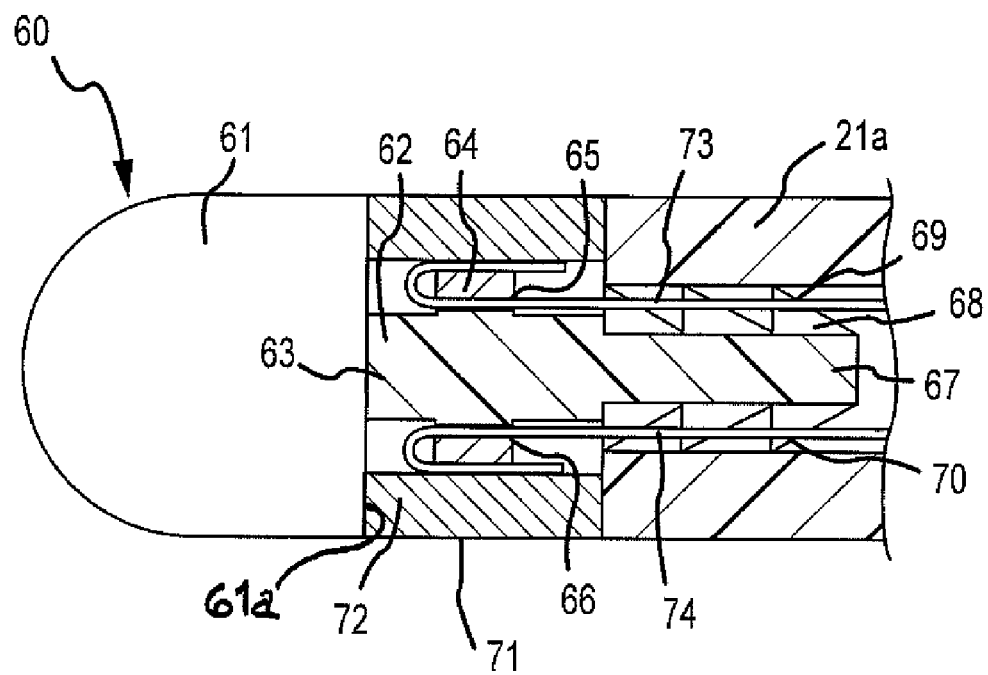
FIG. 4 is a side view, partly in section, of a distal end portion of a catheter shaft, a pull ring assembly and a distal tip according to a second embodiment of the invention.

Turning now to the embodiment of FIG. 4, the distal tip 60 includes a specialized tip element 61 (in an ablation catheter assembly a tip electrode) and a mounting shaft 62 having a distal portion 63 and a proximal portion 67. The proximal portion 67 includes barbs 68 in its outer surface to grip the distal end of the catheter shaft 21a, and axial grooves (guide channels) 69, 70 at diametrically opposed locations. The barbs could be replaced by surface protrusions of varying configurations. The distal portion 63 includes an annular flange 64 having axial guide channels 65 and 66 therethrough which are aligned with axial grooves 69 and 70. The pull ring 72 of pull ring assembly 71 is positioned between the distal end of catheter shaft 21a and an outer annular ledge 61a of the tip element 61, and the pull wires 73 and 74 attached to diametrically opposed locations on its inner face extend toward the tip electrode and then loop back through respective guide channels 65, 69 and 66, 70 to a handle actuator.

Figure 5:
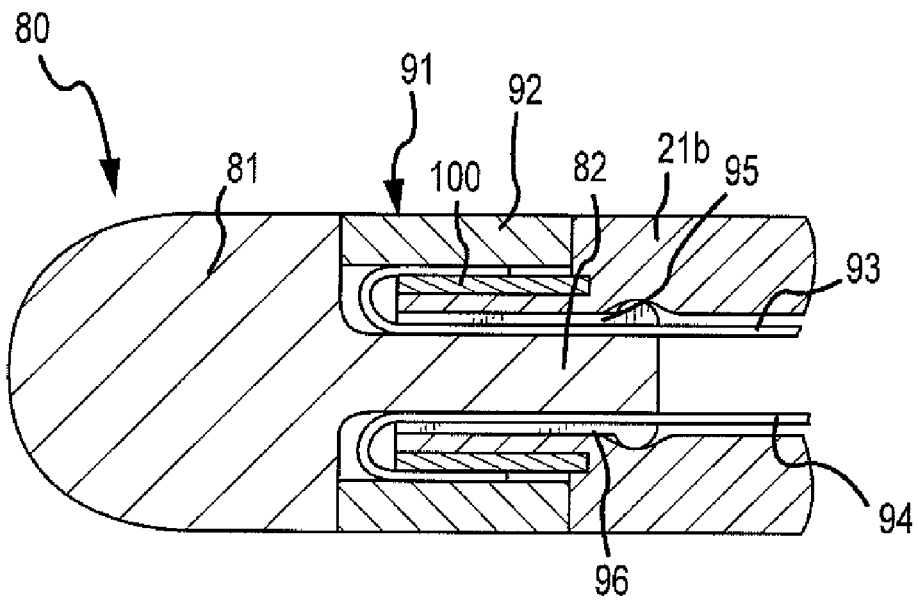
FIGS. 5 and 6 show side views of third and fourth embodiments.

In the embodiment of FIG. 5, a compression ring 100 compresses a distal end portion of catheter shaft 21b against an outer surface of mounting shaft 82, which is one-piece with the tip element 81, and the pull wires 93 and 94 of pull ring assembly 91 extend toward the tip element 81 of distal tip 80 and then loop back toward the catheter shaft and pass through respective axial grooves (guide channels) 95, 96 in the outer surface of the mounting shaft. The compression ring 100 has a generally rectangular cross-section.

Figure 6:
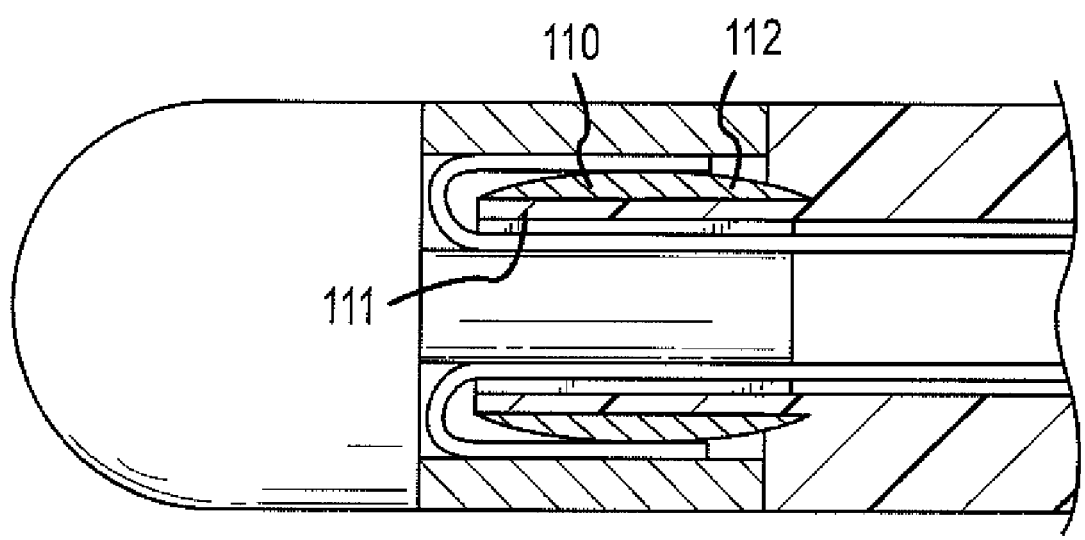

In the embodiment of FIG. 6, which is similar to that of FIG. 5, the compression ring 110 defines a generally flat surface 111 facing inwardly toward the mounting shaft and a generally convex outwardly facing surface 112.

Although a detailed explanation of various embodiments of the invention have been provided, changes therein can be made and still fall within the scope of the present invention. For example, the pull ring assembly may include more than two pull wires attached to the pull ring around its circumference, with corresponding guide channels provided in the distal tip to guide the individual pull wires first toward the tip element of the distal tip and then to loop back to the handle actuator. Also, the compression ring as shown in FIGS. 5 and 6 could have shapes other than those specifically depicted.

What is claimed is:

1. A medical catheter assembly which comprises:
   a deflectable catheter shaft defining a distal end and a hollow interior;
   a distal tip at said distal end of said catheter shaft and including a tip element and a mounting shaft which extends into said hollow interior of said catheter shaft; and
   a pull ring assembly comprising a pull ring and pull wires attached thereto, said pull ring being positioned around said mounting shaft;
   said distal tip providing guide channels through which said pull wires are respectively guided so as to initially extend from said pull ring toward said tip element and then loop back toward and through said catheter shaft, such that pulling of said pull wires directly imparts force to both said pull ring and said distal tip to bend said catheter shaft.

2. The medical catheter assembly of claim 1, wherein said mounting shaft includes an outwardly-extending annular flange having axially-extending passageways therethrough which comprise said guide channels.

3. The medical catheter assembly of claim 2, wherein said mounting shaft includes a distal portion connected to said tip element and a proximal portion which extends into said catheter shaft, wherein said outwardly-extending annular flange is one piece with said distal portion, and wherein said proximal portion includes surface protrusions to grip said catheter shaft.

4. The medical catheter assembly of claim 3, wherein said surface protrusions comprise barbs.

5. The medical catheter assembly of claim 4, wherein axial grooves are provided in said barbs in alignment with said axial passageways and comprise said guide channels.

6. The medical catheter assembly of claim 1, including a compression ring which compresses a distal end portion of said catheter shaft against an outer surface of said mounting shaft.

7. The medical catheter assembly of claim 6, wherein said outer surface of said mounting shaft includes axial grooves therein which comprise said guide channels.

8. The medical catheter assembly of claim 7, wherein said catheter shaft further includes a proximal end and an axis extending from said proximal end to said distal end, wherein said compression ring has a generally rectangular axial cross section.

9. The medical catheter assembly of claim 7, wherein said compression ring has a generally flat surface facing inwardly toward said mounting shaft and a generally convex outwardly facing surface.

10. The medical catheter assembly of claim 1, wherein said tip element defines an outer annular ledge and said pull ring is located between said catheter shaft and said outer annular ledge.

11. The medical catheter assembly of claim 1, wherein said distal tip includes two guide channels on diametrically opposite sides thereof.

12. The medical catheter assembly of claim 11, wherein said pull ring assembly includes two pull wires attached to diametrically opposite locations on said pull ring.

13. The medical catheter assembly of claim 1, wherein each pull wire is flat along at least a portion of its length.

14. The medical catheter assembly of claim 1, wherein each pull wire is connected to an inner surface of said pull ring.

15. The medical catheter assembly of claim 14, wherein each pull wire is connected to said pull ring by a weld.

16. An ablation catheter assembly which comprises:
a deflectable catheter shaft defining a distal end and a hollow interior;
a distal tip at said distal end of said catheter shaft and including a tip electrode and amounting shaft which extends into said catheter shaft;
a pull ring assembly comprising a pull ring and pull wires attached thereto, said pull ring being positioned around said mounting shaft;
said distal tip providing guide channels through which said pull wires are respectively guided so as to initially extend from said pull ring toward said tip electrode and then loop back toward and through said catheter shaft, such that pulling of said pull wires to cause said pull ring to bend said catheter shaft will directly impart force to both said pull ring and said distal tip and will cause said pull ring to interlock with said tip electrode.

17. The ablation catheter assembly of claim 16, wherein said distal tip includes a fluid manifold between said tip electrode and said mounting shaft, and wherein each of said guide channels includes a curved section and a rectilinear section in said mounting shaft.

18. The ablation catheter assembly of claim 17, comprising two guide channels on diametrically opposite sides of said distal tip, and wherein said pull ring assembly includes two pull wires attached to diametrically opposite locations on said pull ring.

19. The ablation catheter assembly of claim 17, wherein said mounting shaft and said tip electrode are one piece.

20. The ablation catheter assembly of claim 16, wherein each pull wire is flat along at least a portion of its length.

21. The ablation catheter assembly of claim 16, wherein each pull wire is connected to an inner surface of said pull ring.

22. An assembly for attachment to a catheter shaft having a distal end and a hollow interior, the assembly comprising:
a distal tip comprising a tip electrode and a mounting shaft, said mounting shaft defining guide channels that first extend distally toward said tip electrode and then loop away from said tip electrode and extend proximally, said mounting shaft configured to extend into said catheter shaft hollow interior; and
a pull ring assembly configured to be disposed at said catheter shaft distal end, said pull ring assembly comprising a pull ring positioned around said mounting shaft and pull wires connected to said pull ring, said pull wires extending through said guide channels such that pulling of said pull wires causes said pull ring to interlock with said tip electrode.

* * * * *

UNITED STATES PATENT AND TRADEMARK OFFICE
CERTIFICATE OF CORRECTION

PATENT NO. : 8,162,934 B2
APPLICATION NO. : 11/963441
DATED : April 24, 2012
INVENTOR(S) : Daniel J. Potter It is certified that error appears in the above-identified patent and that said Letters Patent is hereby corrected as shown below:

Column 5, claim 16, line 5, kindly delete "amounting" and replace with --a mounting--.

Signed and Sealed this
Nineteenth Day of March, 2013

Teresa Stanek Rea
*Acting Director of the United States Patent and Trademark Office*